(12) United States Patent
Wallace et al.

(10) Patent No.: US 8,843,216 B2
(45) Date of Patent: Sep. 23, 2014

(54) CONTROL OF SHAPE OF AN IMPLANTABLE ELECTRODE ARRAY

(75) Inventors: Gordon Wallace, Gwynneville (AU); Geoff Spinks, Balgownie (AU); Dezhi Zhou, East Melbourne (AU); Claudiu Treaba, Wollstonecraft (AU); Peter Gibson, South Coogee (AU); Elaine Saunders, Hampton East (AU); Jin Xu, Doncaster (AU); Robert Cowan, Prahan (AU)

(73) Assignee: Cochlear Limited, Macquarie University, NSW (AU)

( * ) Notice: Subject to any disclaimer, the term of this patent is extended or adjusted under 35 U.S.C. 154(b) by 2812 days.

(21) Appl. No.: 10/498,116

(22) PCT Filed: Dec. 10, 2002

(86) PCT No.: PCT/AU02/01660
§ 371 (c)(1),
(2), (4) Date: Mar. 22, 2005

(87) PCT Pub. No.: WO03/049658
PCT Pub. Date: Jun. 19, 2003

(65) Prior Publication Data
US 2010/0268312 A1  Oct. 21, 2010

(30) Foreign Application Priority Data
Dec. 10, 2001 (AU) ........................ PR9362

(51) Int. Cl.
*A61N 1/36* (2006.01)
*A61N 1/02* (2006.01)
*A61F 11/04* (2006.01)
*A61N 1/05* (2006.01)

(52) U.S. Cl.
CPC .............. *A61F 11/04* (2013.01); *A61N 1/0541* (2013.01); *A61N 1/36032* (2013.01)
USPC ............... 607/137; 607/136; 607/55; 607/56; 607/57

(58) Field of Classification Search
CPC ... A61N 1/36032; A61N 1/0541; A61F 11/04
USPC ...................... 607/55–57, 136, 137
See application file for complete search history.

(56) References Cited

U.S. PATENT DOCUMENTS

| | | | |
|---|---|---|---|
| 5,771,902 A | 6/1998 | Lee et al. | |
| 5,800,500 A * | 9/1998 | Spelman et al. | 607/137 |
| 6,304,787 B1 * | 10/2001 | Kuzma et al. | 607/137 |

FOREIGN PATENT DOCUMENTS

| | | |
|---|---|---|
| JP | 2000-133854 | 5/2000 |
| WO | WO 96/31087 | 10/1996 |

(Continued)

OTHER PUBLICATIONS

Baughman, RH, Cui, C, Zakhidov, AA, Iqbal, Z, & Barisci, JN. (1999). Carbon nanotube actuators. Science, 284, 1340-1344.*

(Continued)

*Primary Examiner* — Tammie K Heller
(74) *Attorney, Agent, or Firm* — K&L Gates LLP (57) ABSTRACT

An implantable electrode array includes an elongated carrier (20) and a plurality of electrodes mounted within the carrier. A actuator adjusts the curvature of the carrier and can be controlled by varying an electric potential applied to the actuator. The actuator is based on an electrochemical cells and may be a conducting polymer based actuator.

39 Claims, 7 Drawing Sheets

(56) References Cited

FOREIGN PATENT DOCUMENTS

| | | |
|---|---|---|
| WO | WO 97/06760 | 2/1997 |
| WO | WO 00/78222 | 12/2000 |
| WO | WO 02/074211 | 9/2002 |

OTHER PUBLICATIONS

Smela et al, "Electrochemically Driven Polypyrrole Bilayers for Moving and Positioning Bulk Micromachined Silicon Plates," *Journal of Microelectromechanical Systems.* vol. 8, No. 4, Dec. 1999.

\* cited by examiner

CONTROL OF SHAPE OF AN IMPLANTABLE ELECTRODE ARRAY

CROSS-REFERENCE TO RELATED APPLICATIONS

This application is a national stage application PCT/AU02/01660, filed on Dec. 10, 2002, which claims the priority of AU Patent No. PR 9362, filed on Dec. 10, 2001. The entire disclosure and contents of the above patents and applications are hereby incorporated by reference.

FIELD OF THE INVENTION

The present invention relates to a novel way of controlling the shape of an implantable conductor element during and following a surgical insertion procedure. The present invention is also directed to a novel way of steering an implantable conductor element during and following a surgical insertion procedure. More preferably, the present invention relates to a novel way of controlling the shape of a cochlear electrode array during and following surgical insertion to ensure that the array is positioned as close as possible to the modiolus and that the insertion process does not damage the sensitive structures of the cochlea. The present invention is also directed to an associated implantable cochlear electrode assembly.

BACKGROUND OF THE INVENTION

Implantable electronic medical devices and systems have been in use for a considerable period of time. One of the earliest implantable medical devices to be implanted in a recipient was a cardiac pacemaker. Other implanted electronic devices include neurostimulators, implantable sensors, defibrillators and cochlear implants. Common to all types of implantable electronic devices is the requirement that at least one electrical lead is connected thereto in order for the device or system to perform its intended function. Such a lead(s) typically terminate in one or more electrodes designed to be in contact with body tissue to deliver stimulation thereto or to sense the condition thereof.

Cochlear implants are an effective way to restore the sensation of hearing to individuals who suffer from a severe or profound hearing loss. In such cases cochlear implants bypass the hair cells of the cochlea which may be damaged or absent, and directly deliver electrical stimulation to the auditory nerve fibres of the cochlea which is representative of external sound. This electrical stimulation is then sent to the brain where it is perceived as sound.

The electrical stimulation is usually delivered by a plurality of electrodes which are inserted into the cochlea and which are strategically positioned therein, to target specific regions of the cochlea to deliver the electrical stimulation. Each of these electrodes is connected to a central implantable stimulator via a wire or wires. The implantable stimulator receives signals from an external speech processor that provide direction regarding which electrode needs to be stimulated and at what frequency and amplitude. The implantable stimulator then sends the appropriate stimulation to the appropriate electrode to reproduce the desired sound sensation.

A considerable amount of research has been undertaken in the area of understanding the way sound is naturally processed by the human auditory system. With such an increased understanding of how the cochlea naturally processes sounds of varying frequency and magnitude, it has been possible to identify areas of improvement in delivering electrical stimulation to the auditory nerve to take into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the cilia disposed on the modiola of the cochlea. Several electrodes may be active simultaneously.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the shape of the modiola and must also be shaped such that the insertion process causes minimal trauma to the sensitive structures of the cochlea. In this sense it has been found to be desirable for the electrode array be generally straight during the insertion procedure.

Several procedures have been adopted to provide an electrode assembly that is relatively straightforward to insert while adopting a curved configuration following insertion in the cochlea. In one case, a platinum wire stylet is used to hold a pre-curved electrode array in a generally straight configuration up until insertion. Following insertion, the platinum stylet is withdrawn allowing the array to return to its pre-curved configuration.

Other methods have also been proposed and implemented with varying degrees of success. Such methods include constructing the array in a straight configuration and inserting positioners with the electrode array to force the array into its final position close to the modiolus. Such positioners may be designed to fill up the space within the cochlea and behind the array, so that the array is forced against the inner wall of the cochlea. Examples of such designs can be seen in U.S. Pat. Nos. 6,195,586 and 6,163,729. It is considered that such methods are not ideal as they are invasive and tend to damage the sensitive structures of the cochlea, and should there be a need to remove the electrode array from the cochlea, it would be difficult to do so with such devices without causing severe damage to the cochlea.

Other methods of achieving close positioning of the array to the inner wall of the cochlea have been proposed which utilise bioresorbable polymers and the like which swell upon contact with fluid to force the array into position. Also there are other methods which utilise a dissolvable layer which dissolves upon contact with fluid to release positioning fins to assist in positioning the array. Such methods are shown in U.S. Pat. No. 5,653,742. One problem with such methods is that it is difficult to control the dissipation/swelling of the bioresorbable polymers and as such full and total control of the shape of the array during insertion is difficult to achieve.

The present invention aims to improve on the above mentioned prior art by providing a cochlear implant array that is capable of being shaped controlled during the insertion process so that the array can achieve close positioning to the modiolus as well as achieving minimal damage to the sensitive structures of the cochlea.

In other types of implantable medical devices, particularly cardiac pacemakers and neurostimulators, the electrodes must be strategically positioned in the body close to desired stimulation sites, namely heart tissue or nerve sites. In this regard it is important that if the electrode requires passing through tissue or regions of the body such as arteries or veins, the shape of the electrode element be controlled to ensure that this occurs without considerable damage to the surrounding tissue. In another aspect therefore, the present invention aims to provide an implantable conductor that is capable of being shape controlled or steered during the insertion process so that the array can be strategically position close to the desired stimulation site without causing surrounding damage to the surrounding tissue.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

SUMMARY OF THE INVENTION

In one broad aspect the invention utilises an actuator which can be controlled, typically by varying an electric potential applied to the actuator, to adjust the curvature of an implantable element such as an electrode array.

The actuator may be based on an electrochemical cell and may in particular be a polymer actuator which relies on the actuating properties of inherently conducting polymers. Other suitable electrochemical cell type actuators includes carbon nanotubes.

More specifically, in a first aspect, the present invention provides an implantable electrode array assembly including:

an elongated carrier having a proximal end, a distal end, and an inner surface;

a plurality of electrodes mounted within the carrier at least one of the electrodes having a surface that is at least adjacent the inner surface of the carrier; and an actuator for adjusting the curvature of the carrier whose curvature is adjustable by the application of an electric potential to the actuator and whose curvature may be varied by varying the electric potential.

In a preferred embodiment the actuator is an electrochemical actuator and most preferably a polymer actuator which incorporates an inherently conducting polymer. Such polymer actuators can be constructed on both micro and macro scales and can be viewed as simple electromechanical cells in which the application of a potential creates dimensional changes in one or more of the electrode materials.

In an alternative embodiment, the electrochemical actuator is based on carbon nanotubes.

In a preferred embodiment the plurality of electrodes is designed to conform with the inner wall of the cochlear and the assembly is preformed into a curved configuration and the polymer actuator provides the force to maintain the assembly in the straight configuration which is the preferred configuration for the insertion of the assembly. Preferably, the curved configuration is such that the carrier can fit inside the cochlea of the implantee with said adjacent surfaces of the electrodes being oriented to face the modiolus of the cochlea However in another embodiment it would be possible for the assembly actuator to be straight and the electric potential is used to apply curvature to the array to position it appropriately.

In yet another embodiment, the electrode assembly could be made in a pre-curved shape with the spiral actuator, moulded inside the assembly structure. In this embodiment the actuator could be used to perform the final positioning of the array, to push the shape recovery to the 'ideal'—then disconnect.

The polymer actuator may be in the form of a tube comprising an inherently conducting polymer. In one embodiment, the polymer tube may comprise polypyrrole with hexafluorophosphate as dopant.

The tube may incorporate a helically wound conducting wire, such as platinum and have its ends sealed with electrodes, typically platinum electrodes.

A related aspect the invention provides a method of inserting a cochlear implant electrode array as described above into a cochlear by varying the electric potential applied to the actuator during the insertion of the electrode.

In a yet further embodiment the actuator could incorporate light sensitive gels in the form of a bimorph or other actuator array which actuator may be caused to curve when light is applied to the actuator to either straighten a pre-curved cochlear implant electrode array or curve a straight or pre-curved cochlear implant array.

In a first embodiment, each of the electrodes in the array have a surface that is at least adjacent the inner surface of the carrier. In a further embodiment, the surfaces of the electrodes are aligned with the inner surface of the carrier. In another embodiment, the surfaces of the electrodes stand proud of the inner surface of the carrier. It is also envisaged that the electrode surface could also be recessed into the inner surface of the carrier.

To avoid bio-incompatibility of the electrode, the outer layer of the electrode preferably comprises a medical grade elastomeric material. In one embodiment, the elastomeric material can be a silicone rubber. In another embodiment, the elongate member can be formed from a polyurethane or similar material.

In a preferred embodiment, the implantable electrode array is a cochlear implant electrode array, with the carrier being adapted for insertion into the cochlea of an implantee. Preferably, the carrier is adapted for insertion into the scala tympani of the cochlea of the implantee.

The outer surface of the second layer of the carrier is preferably smooth to prevent any damage to the cochlea as the carrier is inserted into the cochlea.

In a preferred embodiment, the electrode array can include electrically conducting wires connected to the electrodes and extending to at least said proximal end. In one embodiment, one wire can be connected to each of said electrodes. In another embodiment, at least two wires can be connected to each of said electrodes.

Each electrode can comprise a contact member. The carrier can have a longitudinal axis with each contact member arranged orthogonally to the longitudinal axis. The contact members can be formed from a bio-compatible material. The bio-compatible material can be platinum. The wires are preferably connected to the contact members by welding.

The carrier of the electrode array preferably naturally adopts a spiral configuration. In a preferred embodiment, the spiral carrier subtends an arc greater than 450°.

In one embodiment the actuator is embedded in the electrode array. Alternatively the actuator may be attached to one side of the electrode array.

In yet a further embodiment, the actuator can act as a substance delivery means for delivering a bio-active substance to the implant site following implantation.

The bio-active substance may be present as a dopant in the polymer.

Alternatively the actuator may define a lumen or other reservoir for the bio-active substance. In one embodiment, the bio-active substance can leach from the polymer into the surrounding material of the carrier and eventually migrate to an outer surface of the carrier, that is preferably close to the desired site of action for the bio-active substance. In another embodiment, the carrier can have one or more substance egress means whereby the bio-active substance can move out of the lumen and through the carrier to a position that is preferably close to the desired site of action for the bio-active substance.

Where the bio-active substance is carried in, or comprises, a fluid, each substance egress means preferably comprises a fluid egress means.

Each fluid egress means preferably has a valve means that allows fluid to exit the lumen but prevents, or at least substantially prevents, fluid flow from external the elongate member back into the lumen within the carrier.

In a further embodiment, the proximal opening of the lumen can be in fluid communication with an additional reservoir for the bio-active substance that is external to the carrier. A pumping means, such as an osmotic pump, can transfer the bio-active substance from the additional reservoir into the lumen of the carrier for subsequent delivery to the appropriate site of action.

In one embodiment, the bio-active substance can comprise a steroid. In another embodiment, the bio-active substance can perform a function of reducing the resting neuron potential of neurons within the cochlea. The use of such substances can result in less energy being required to excite the neurons and cause stimulation.

In a still further embodiment, at least a portion of the outer surface of the carrier can have a coating of lubricious material. In a further embodiment, a substantial portion of the outer surface can have a coating of the lubricious material. In a still further embodiment, the entire outer surface of the carrier can have a coating of the lubricious material.

The lubricious material preferably becomes lubricious on being brought into contact with a fluid, such as a saline solution. Still further, the coating preferably becomes lubricious on being brought into contact with a body fluid, such as cochlear fluid.

The lubricious material is selected from the group consisting of polyacrylic acid (PAA), polyvinyl alcohol (PVA), polylactic acid (PLA) and polyglycolic acid (PGA). It is envisaged that other similar materials could also be used. It is envisaged that the lubricious material can also be impregnated with the bio-active substance allowing the coating to perform a dual role. The rate of delivery of the bio-active substance can be programmed by design of the coating structure.

The present invention provides a surgeon with an implantable conductor element that can be shape controlled and steered during the insertion process.

In another embodiment, the present invention provides a surgeon with a cochlear implant electrode array that can potentially be inserted to a greater degree than hitherto known electrode arrays whilst maintaining close proximity between the surfaces of the electrodes and the modiolus. The increased insertability of the implant electrode array is due in part to the fact that the curvature of the actuator may be predictably varied by varying the electric potential applied to the actuator.

BRIEF DESCRIPTION OF THE DRAWINGS

Specific examples of the present invention will now be described, by way of example only, and with reference to the accompanying drawings, in which:—

PREFERRED MODES OF CARRYING OUT THE INVENTION

Whilst the present invention is applicable to any type of implantable device, it will be described in relation to its application to a cochlear implant.

Figure 1:
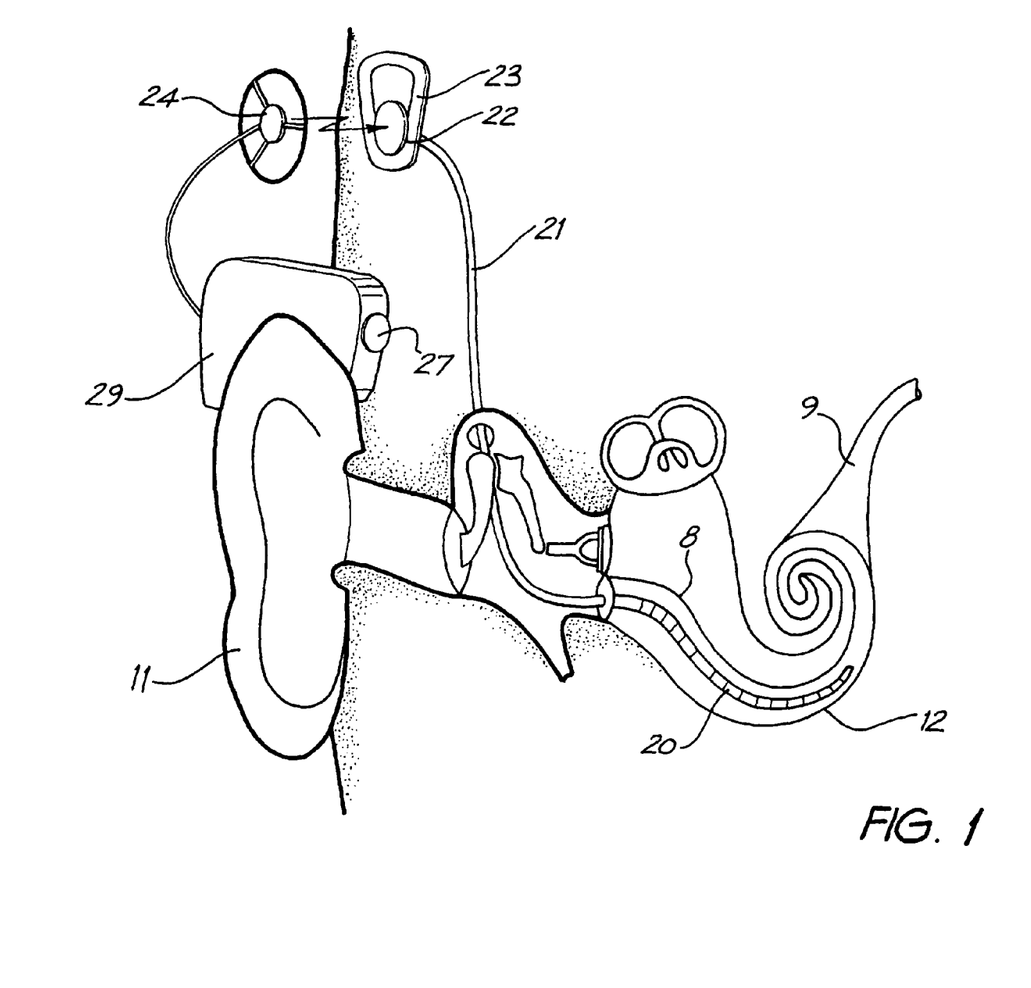
FIG. 1 is a pictorial representation of a prior art cochlear implant system.

Before describing the features of the present invention, it is appropriate to briefly describe the construction of one type of known cochlear implant system with reference to FIG. 1.

Known cochlear implants typically consist of two main components, an external component including a speech processor 29, and an internal component including an implanted receiver and stimulator unit 22. The external component includes a microphone 27. The speech processor 29 is, in this illustration, constructed and arranged so that it can fit behind the outer ear 11. Alternative versions may be worn on the body. Attached to the speech processor 29 is a transmitter coil 24 which transmits electrical signals to the implanted unit 22 via an RF link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is described, for example, in U.S. Pat. No. 4,532,930.

As depicted diagrammatically in FIG. 1, the cochlear implant electrode array 20 has traditionally been inserted into the initial portion of the scala tympani of the cochlea 12 up to about a full turn within the cochlea. The electrode array according to the present invention is adapted to be inserted more deeply into the cochlea 12 than has historically been the case. For the purpose of the remainder of the specification, one embodiment of a cochlear implant electrode array is depicted generally at 10 in FIG. 3 et al.

Polymer actuators are based on polymer materials and can be constructed on both micro and macro scales and can be viewed as simple electromechanical cells in which the application of a potential creates dimensional changes in one or more of the electrode materials. The principles of polymer actuators can be understood ewe consider a polymer gel (a crosslinked polymer chain swollen in a solvent) and how a polymer gel responds to a change in environmental parameters such as temperature and electric fields, often by a change in volume. The changes in the environmental parameters disturb the equilibrium between the gel and the solvent, resulting in the volume change. Conducting polymers have a large electronic conductivity as such polymers contain a conjugated, often one dimensional backbone and their properties usually depend crucially on being oxidised or reduced by the introduction of anions or cations as dopants associated with the chain. The accommodation of ions in the polymer also has consequences for their mechanical properties. The creation of charged electronic species on the chain can change the stiffness and the length of the individual polymer chains, and the incorporation of the sometimes bulky counterions can increase the volume—especially when the ions are associated with co-intercalating solvent molecules. This opens the possibility for the reversible control of mechanical properties by the application of a voltage, and is the foundation for conducting polymers to function as electromechanical actuators.

Figure 2A:
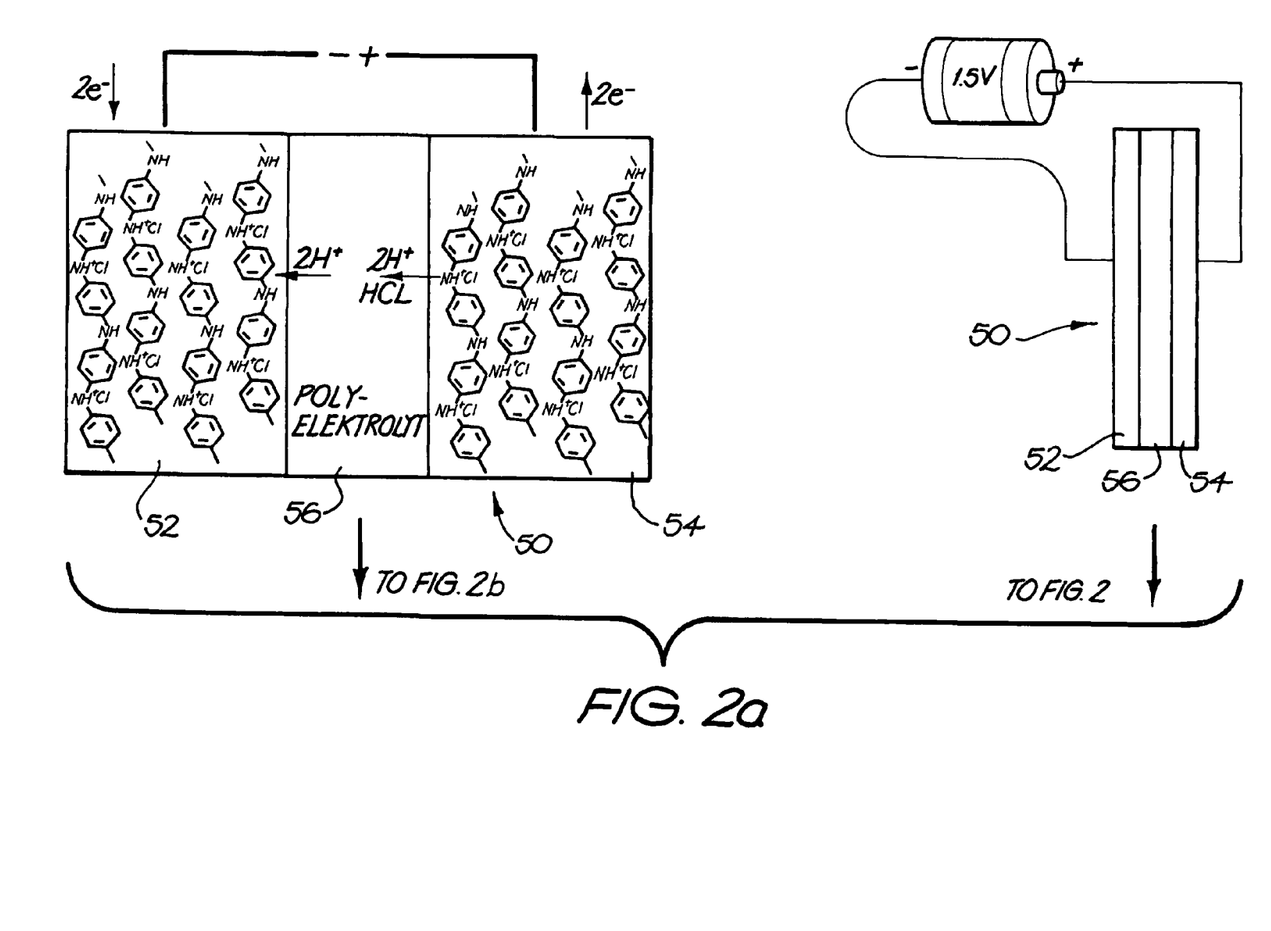
FIGS. 2a and 2b are schematic diagrams of a polymer actuator in a first and a second orientation, respectively.
Figure 2B:
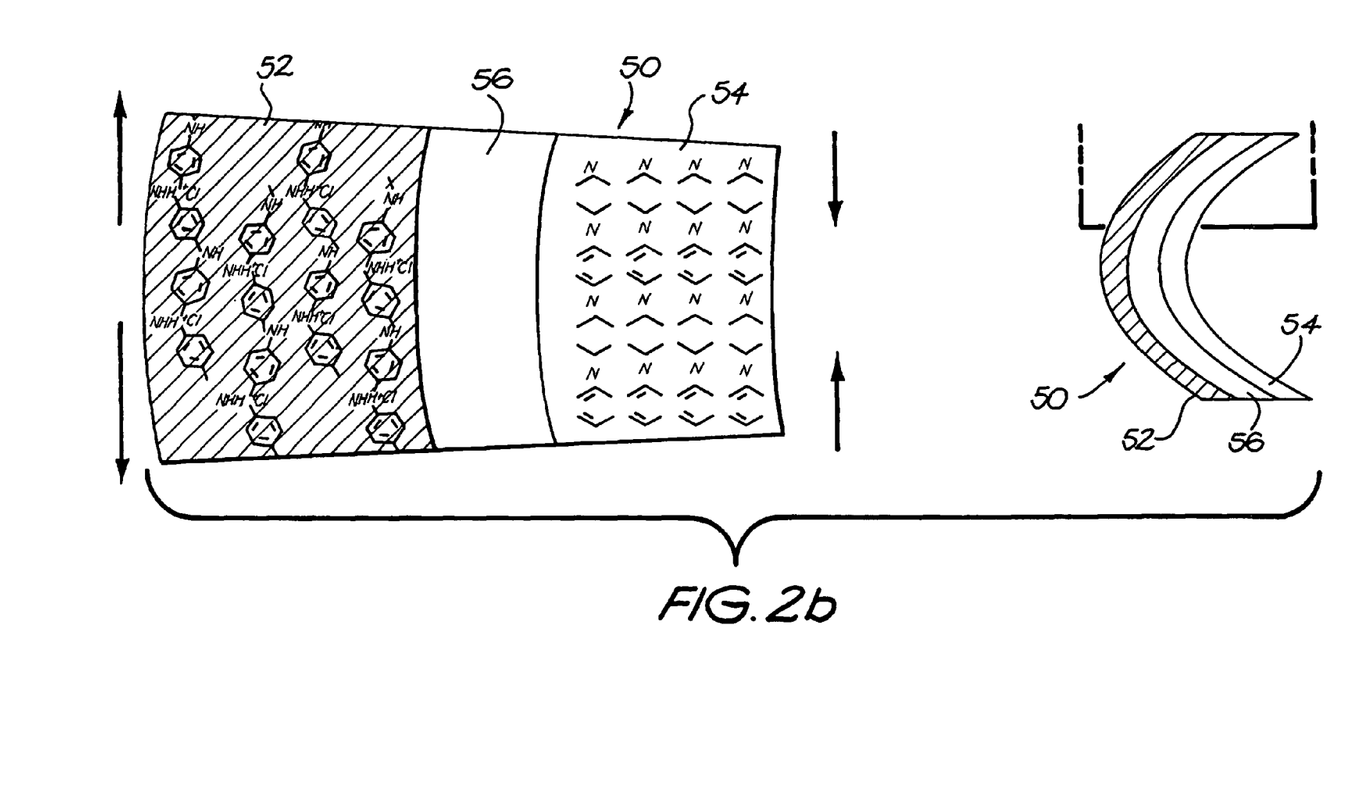

An example of a polymer actuator applicable to the present invention is shown diagrammatically in FIGS. 2a and 2b. In this example a bimorph 50 is based on a conducting polymer polyaniline (Pani) and both the macroscopic and molecular changes in the actuator are shown in this depiction. Two polyaniline films 52, 54 are sandwiched around an ion-conducting film 56. As current flows and a potential is applied to the structure, one side of the sandwich is reduced and the other oxidised. Concurrently, ions are transferred between the two sides leading to an expansion of the first and a contraction of the second side. The overall effect is a bending of the bimorph.

The present invention relates to the application of a controllable actuator mechanism such as a polymer actuator structure described above, to assist in the positioning of a intracochlear electrode array.

Figure 3:
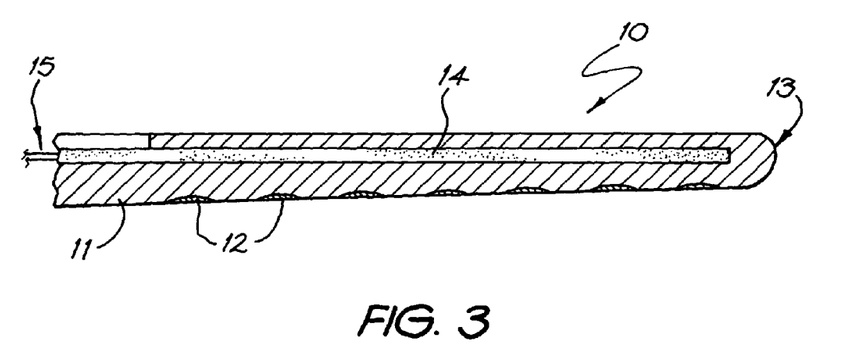
FIG. 3 shows a diagrammatical representation of an electrode array according to one embodiment of the present invention.

FIG. 3 shows a diagrammatical representation of an electrode array according to one embodiment of the present invention. The assembly 10 comprises an elongate electrode carrier member 11 having a plurality of electrodes 12 mounted thereon. For the purposes of clarity, the electrodes 12 depicted in FIG. 2 are not necessarily shown to scale.

The depicted elongate member 11 is preformed from a resiliently flexible silicone with memory and is preformed to a curved configuration suitable for insertion in the scala tympani of the cochlea. The elongate member 11 has a first end or tip 13 that is firstly inserted into the implantee on insertion of the assembly 10.

Disposed within the elongate carrier 11, and preferably embedded within a lumen in the elongate carrier, is an elongate polymer actuator 14 of the type discussed above, and as described in more detail below. The actuator has leads 15 capable of being connected to a current source so that a potential can be applied across the actuator. The polymer actuator can be made from polypyrrole or another suitable conducting polymer and supporting electrolyte. In a preferred embodiment the assembly is preformed into a curved configuration and the polymer actuator provides the force to maintain the assembly in the straight configuration depicted in FIG. 3, which is the preferred configuration for the insertion of the assembly 10. Therefore prior to implantation a potential is applied across the leads 15 so that the actuator 14 works against the natural curvature of the assembly to straighten the assembly.

Figure 4:
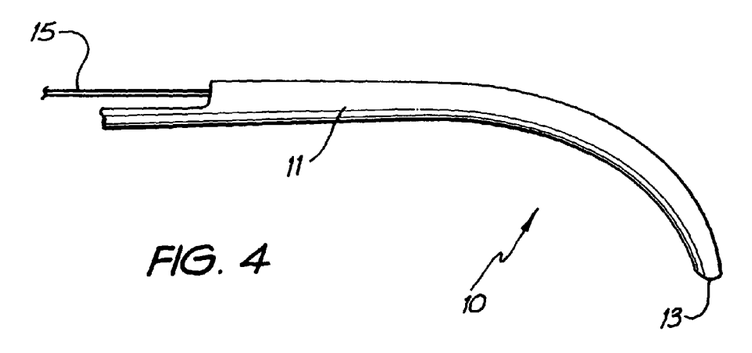
FIG. 4 shows the array of FIG. 3 in a second configuration.

On insertion of the device 10 into the scala tympani of the cochlea 30 and when the first end 13 reaches the back of the basal turn, the amount of potential applied to the conductive polymer structure can be varied so that the elongate member 11 commences to re-curl (see FIG. 4) with the lesser potential applied to the conductive polymer structure holding the device 10 in a more curved shape to assist in the insertion procedure and for the device 10 to assume a mid-scala trajectory during the procedure.

Figure 5:
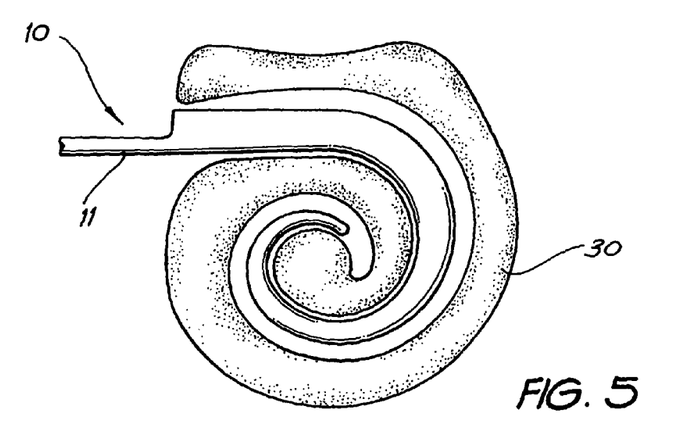
FIG. 5 shows the array of FIG. 3 inserted into a patient's cochlear and generally configured to the shape of the cochlear.

By continually varying the amount of potential applied to the conductive polymer structure, the surgeon can continue to further insert the curled assembly 10 into the scala tympani until the desired insertion is attained. In this manner the surgeon has control of the shape of the assembly 10 throughout the insertion procedure and upon desired insertion, the applied potential can be removed from the conductive polymer whereby the elongate member 11 is free to adopt the spiral configuration depicted in FIG. 5 with the electrodes 12 facing the modiola within the cochlea 30 so that they are positioned as close as possible to the spiral ganglia thereof. In a preferred embodiment, following removal of the applied potential and the array returning to its pre-curved shape, an additional potential may be applied to ensure that the shape recovery is ideal and the array is optimally positioned close to the inner wall of the cochlea.

The provision of greater control over the shape of the assembly throughout insertion minimises the potential for trauma to the sensitive tissues inside the cochlea and also enhances the likelihood of successful placement of the assembly 10 at the first attempt. The present invention also provides for an easy method of removal of the electrode array should there be a need to remove the array from the cochlear. By re-applying a potential across the conductive polymer structure the assembly can be uncurled to a degree to enable the array to be easily removed from the cochlea without damage to the sensitive structures of the cochlea.

The preparation of inherently conducting polymers (ICPs) allows a wide range of compositions to be formed using simple synthetic approaches. Even when using simple polypyrroles a range of chemical/physical properties can be induced by just changing the dopant. In the case of carbon nanotubes and their use as actuators in the present invention, the actuating material is fixed, carbon and consists of a porous mat of tangled nanotubes. However, even with these materials the active electrode normally contains other "trace" impurities either from the production of the carbon nanotubes (CNTs) or deliberately added surfactants/polymers to facilitate CNT dispersion prior to mat/paper preparation.

The requirements of an electrolyte system for use in electromechanical actuators of the present invention are: actuating electrode materials should be stable in this environment; the electrolyte itself should be stable over the potential range required for actuation; non volatile—easily encapsulated; and appropriate mechanical properties. It is possible for electrolytes to be used in an aqueous form such as $NaNO_3$, NaCl, $K_2SO_4$ etc. It is also possible to use solid polymer electrolytes such as polyacrylonitrile and polyethylene oxide One type of conducting polymer actuator suitable for use with the present invention is described in more detail below. A process for manufacturing the actuator is shown in FIGS. 6A to 6G. The actuator is based on a tube configuration as opposed to a flat film. The tube is capable of being inserted into a cochlear electrode assembly or attached to the outer surface of a cochlear electrode assembly. In one embodiment a tubular conducting polymer actuator is constructed. Note that the dimensions and materials of the various components described below are exemplary only, and may be varied according to the particular application for which the actuator is being used.

Figure 6A:
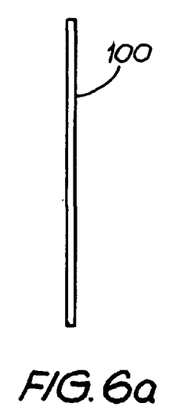
FIGS. 6A to 6G illustrate various steps in a process for manufacturing a polymer actuator embodying the present invention.
Figure 6B:
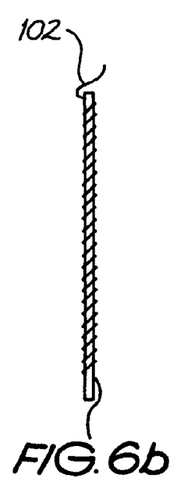
Figure 6C:
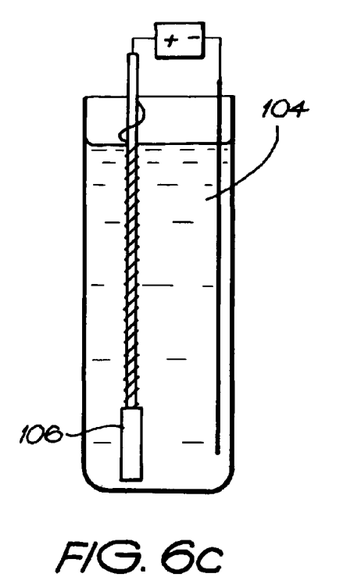
Figure 6D:
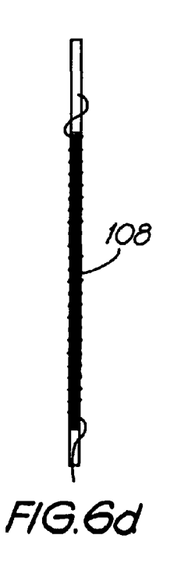

Firstly a 125 micron diameter platinum wire 100 approximately 60 mm long, is provided (see FIG. 6A) and another thinner (typically 25 micron diameter) platinum wire 102 is spirally wound around the wire, as shown in FIG. 6B. Next, as shown in FIG. 6C, the assembly is then placed in a polymer electrolyte solution 104, with a block of insulation 106 covering one end of the wire 100, and electroplated for 24 hours @−28 deg C., wherein a polymer tube 108 forms around the central wire 100 and the spiral wire 102 (see FIG. 6D). In the specific example the electro-deposition was from a solution containing 0.06M pyrrole and 0.05 M $TBAPF_6$ in propylene carbonate id=0.15 $mA/cm^2$. The resultant polymer tube comprised polypyrrole with hexafluorophosphate as dopant.

Figure 6E:
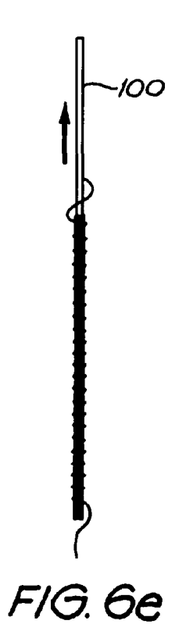
Figure 6F:
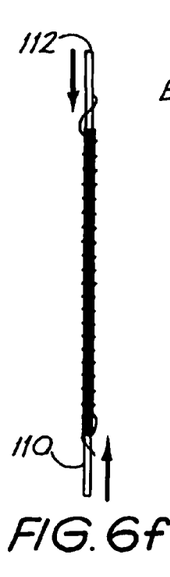
Figure 6G:
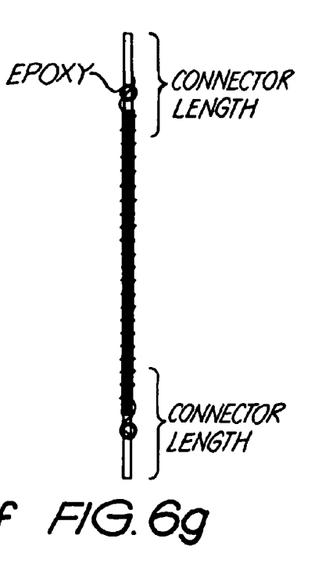

Next, with reference to FIG. 6E, the central wire 100 is then withdrawn from the polymer tube/helix 108 and two short connectors 110 and 112 are inserted into each end of the polymer tube 108. The spiral wire 102 is then pulled tight around the connectors 110 and 112 for good electrical connection and they are glued in place to form the polymer actuator. The polymer actuator 114 made from this process is shown in FIG. 6G.

Figure 7:
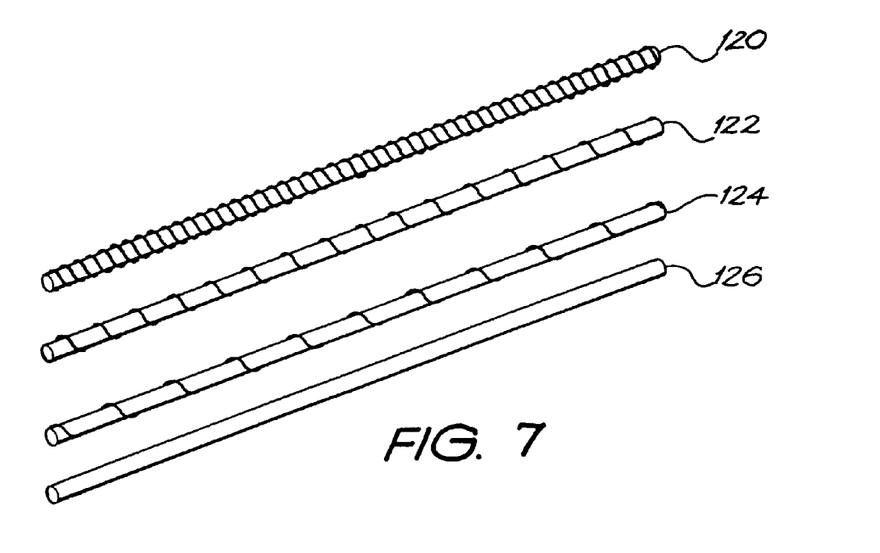
FIG. 7 illustrates a number of polymer actuators having different wired pitches.

FIG. 7 illustrates a number of polymer actuators in which the 25 micron platinum wire is wound at different pitches or omitted altogether. In actuator 120 the wire was wound at 25 turns/cm, actuator 122 at 15 turns/cm, actuator 124 at 10 turns/cm and in actuator 126 the wire 102 is omitted.

Figure 8:
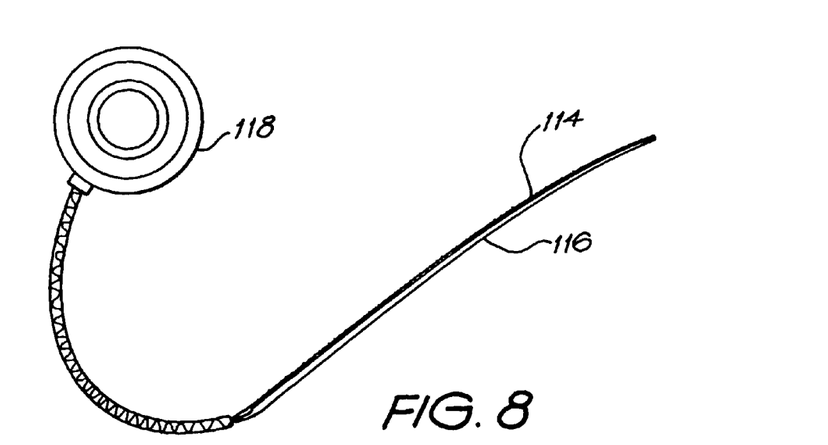
FIG. 8 shows a polymer actuator attached to the side of a cochlear implant.
Figure 9:
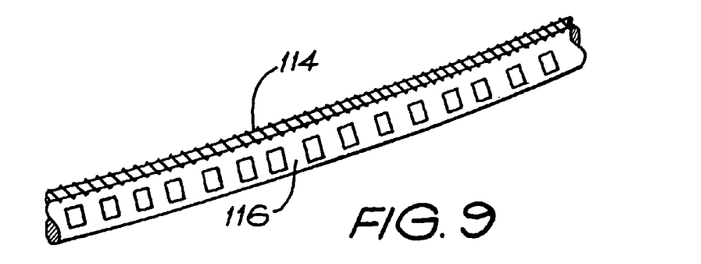
FIG. 9 is a close up of the implant/actuator shown in FIG. 8.

The arrangement described above is a closed system whereby the actuator is isolated from body fluid or tissue by being packaged within the structure of the carrier. In such a closed system the actuator structure must form a complete electrochemical cell and as such a solid electrolyte or other electrolyte is required within the closed structure. It is however possible to design an open system whereby the actuator uses body fluid as part of the electrochemical cell in the actuator system. In such an embodiment the conductive polymer actuator may be removably attached to the surface of the electrode array rather than being embedded therein and there is no need to provide an electrolyte with the actuator, as the body fluid would perform this function. An embodiment in which the actuator 114 is attached to the side of an electrode array 116 is shown in FIGS. 8 and 9 with the electrode attached to a cochlear electrode array 118.

Figure 10:
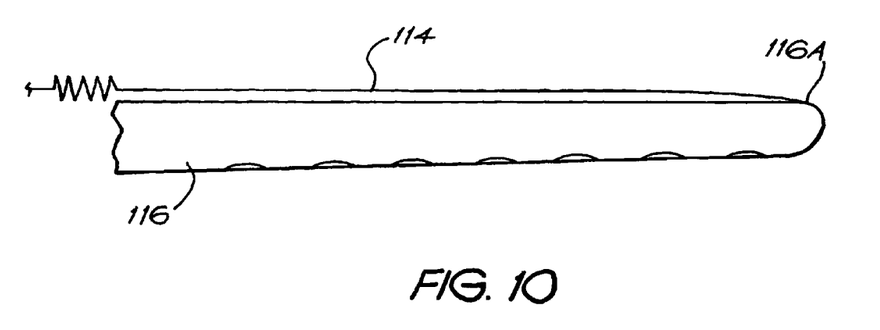
FIG. 10 is a schematic drawing of a further embodiment of an implantable element including an actuator of FIG. 9.
Figure 11:
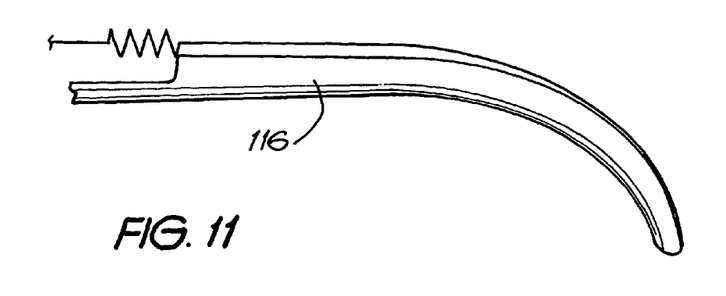
FIG. 11 shows the element of FIG. 10 partly curled.
Figure 12:
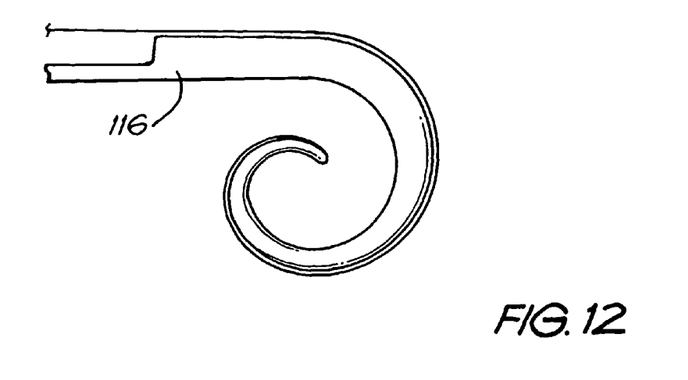
FIG. 12 shows the element of FIG. 11 more fully curled.

FIGS. 10-12 show in more detail an embodiment of the present invention wherein the actuator 114 is attached to the side of an electrode array 116. In this regard, the actuator 114 is in the form of a tendon attached to the tip 116A of the electrode array 116 and extending along the rear surface of the electrode. In this embodiment there is shown only one attachment point at the tip 116A of the electrode, although it can be envisaged that there could be any number of attachment points along the rear surface of the electrode array 116 to ensure the tendon 114 is maintained in correct placement.

The stiffness of the tendon 114 is controlled by axial actuation such that an appropriate potential is applied to the tendon 114 to cause the tendon to contract thereby maintaining the naturally curved electrode array 116 in a substantially straight position as shown in FIG. 10. It should be appreciated that whilst the electrode array shown in FIG. 10 is predominantly straight the actual shape of the array may be slightly curved, as the purpose of straightening the array for insertion is to ensure that the array is easily inserted into the opening of the cochlea.

By altering the potential applied to the tendon, the contraction of the tendon can be reduced thereby allowing the electrode array to assume a more curved configuration as shown in FIG. 11. Such a configuration may be appropriate once the electrode has been inserted beyond the first basal turn of the cochlea to assist the surgeon in "steering" the electrode deeper into the cochlea without damaging the sensitive walls of the cochlea. The potential can be further altered during the insertion procedure by the surgeon to enable the electrode array to assume a more curved configuration as desired.

As shown in FIG. 12, once the electrode array has been inserted to a desired depth the potential can be removed from the tendon allowing the electrode array to assume its natural curved configuration, in this instance, its configuration aimed to correspond with the natural curved shape of the cochlea.

It should be appreciated that whilst the preferred embodiment has been described in relation to cochlear implants, the present invention could also be equally applied to any implantable devices. For example, in functional electrical stimulation (FES) systems aimed at restoring lost function to spinal cord injured patients, there is a requirement that electrodes and leads must be tunnelled under the skin of a recipient to be placed adjacent the desired nerves to be stimulated. The ability to control the shape of the electrode and/or lead during the tunnelling procedure would greatly assist in correctly positioning the electrode array and ensuring that the procedure is as non-invasive as possible. There are also obvious adaptations of the present invention to cardiac pacemakers and stent technology where the ability to control the orientation and shape of the element during surgery would be invaluable to ensure that the elements are inserted correctly within the vein/artery/heart.

Thus the present invention provides an electrode whose shape during insertion into a patient's cochlear, by varying the electric potential applied to the polymeric actuator can be controlled by a surgeon more readily than with prior art systems.

The polymer actuators may also be used for the controlled release of chemicals including bio-active materials which may be present as dopants in the polymer, in combination with the silicone rubber electrode carrier.

In another embodiment, the electrode array could be constructed in a straight configuration and the actuator actually applies the curvature to the array to position it appropriately.

In another embodiment instead of applying an electric potential across the actuator, light sensitive gels could replace the polymers and the actuation could be optically induced.

In a yet further embodiment carbon nanotubes (CNT's) could be used as actuators instead of inherently conducting polymers (ICPs). These electrochemical actuators utilise non-Faradaic electrochemical charging of high surface area electrodes to produce dimensional changes for actuation in covalently bonded directions. Nanotube actuation based on double layer non-Faradaic charge injection can be obtained see R Baughman et al., *Science*. 284, pp. 1340, 1999.

The potential advantages in using CNT actuators compared with ICPs is that CNTs have a modulus ~50 times higher than ICPs which means that the CNT actuators will be able to generate higher stresses than the ICP actuators. In other words, a CNT actuator would occupy less volume in the cochlear array compared with the ICP and still be able to adjust the curvature of the array.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. An implantable electrode array assembly including:
   an elongated carrier having a proximal end, a distal end, and an inner surface;
   a plurality of electrodes mounted within the carrier, at least one of the electrodes having a surface that is adjacent the inner surface of the carrier; and
   an electrochemical actuator which changes chemical structure due to an ionic transfer when an electric potential is applied thereto, the actuator being configured to adjust a curvature of the carrier, wherein the curvature is adjustable by applying the electric potential to the actuator.

2. An implantable electrode array assembly as claimed in claim 1 wherein the actuator is a polymer actuator incorporating an inherently conducting polymer.

3. An implantable electrode array assembly as claimed in claim 2 wherein the polymer actuator is in the form of a tube comprising the inherently conducting polymer.

4. An implantable electrode array assembly as claimed in claim 3 wherein the polymer forming the tube comprises polypyrrole with hexafluorophosphate as dopant.

5. An implantable electrode array assembly as claimed in claim 3 wherein the tube incorporates a helically wound conducting wire.

6. An implantable electrode array assembly as claimed in claim 5 wherein the conducting wire comprises platinum.

7. An implantable electrode assembly as claimed in claim 3 wherein the tube defines ends into which electrodes are inserted to seal those ends.

8. An implantable electrode array assembly as claimed in claim 2 wherein the actuator acts as a substance delivery means for delivering a bio-active substance to an implant site following implantation.

9. An implantable electrode array assembly as claimed in claim 8 wherein the bio-active substance is present as a dopant in the polymer.

10. An implantable electrode array assembly as claimed in claim 9 wherein the bio-active substance is arranged to leach from the polymer into surrounding material of the carrier and subsequently migrate to an outer surface of the carrier.

11. An implantable electrode array assembly as claimed in claim 10 wherein the bio-active substance comprises a steroid.

12. An implantable electrode array assembly as claimed in claim 9 wherein the bio-active substance performs a function of reducing a resting neuron potential of neurons within a cochlea.

13. An implantable electrode array assembly as claimed in claim 1 wherein the actuator includes a carbon nanotube.

14. An implantable electrode array assembly as claimed in claim 1 wherein the plurality of electrodes are designed to conform with an inner wall of a cochlea and the assembly is preformed into a curved configuration and wherein the actuator provides a force to maintain the assembly in a straight configuration when subject to the electric potential.

15. An implantable electrode array assembly as claimed in claim 14 wherein the curved configuration is such that the carrier can fit inside the cochlea of an implantee with said surface of said at least one of the electrodes adjacent the inner surface being oriented to face the modiolus of the cochlea.

16. An implantable electrode array assembly as claimed in claim 1 wherein each of the electrodes in the array has a surface that is adjacent the inner surface of the carrier.

17. An implantable electrode array assembly as claimed in claim 16 wherein the surfaces of the electrodes are aligned with the inner surface of the carrier.

18. An implantable electrode array assembly as claimed in claim 1 wherein the surfaces of the electrodes stand proud of the inner surface of the carrier.

19. An implantable electrode array assembly as claimed in claim 1, wherein each of the electrodes in the array has a surface which is recessed into the inner surface of the carrier.

20. An implantable electrode array assembly as claimed in claim 1 wherein at least one of the electrodes has an outer layer comprising a medical grade elastomeric material.

21. An implantable electrode array assembly as claimed in claim 20 wherein the elastomeric material is a silicone rubber.

22. An implantable electrode array assembly as claimed in claim 1 wherein the implantable electrode array is a cochlear implant electrode array, with the carrier being adapted for insertion into the scala tympani of the cochlea of an implantee.

23. An implantable electrode array assembly as claimed in claim 1 wherein the electrode array includes electrically conducting wires connected to the electrodes and extending to at least said proximal end.

24. An implantable electrode array assembly as claimed in claim 1 wherein each electrode comprises a contact member.

25. An implantable electrode array assembly as claimed in claim 24 wherein the contact members are formed from a bio-compatible material such as platinum.

26. An implantable electrode array assembly as claimed in claim 1 wherein the carrier naturally, in the absence of applying the electric potential, adopts a spiral configuration which subtends an arc greater than 450°.

27. An implantable electrode array assembly as claimed in claim 1 wherein the actuator is embedded in the electrode array.

28. An implantable electrode array assembly as claimed in claim 1 wherein the actuator is attached to one side of the electrode array.

29. An implantable electrode array assembly as claimed in claim 1 wherein the electrochemical actuator is dimensionally changeable by the ionic transfer therein responsive to the application of the electric potential, and wherein dimensional changes in the actuator apply forces to the carrier that adjust the curvature of the carrier.

30. A method of inserting a cochlear implant electrode array into a cochlea, wherein the electrode array comprises an elongated carrier having a proximal end, a distal end, and an inner surface; a plurality of electrodes mounted within the carrier, at least one of the electrodes having a surface that is adjacent the inner surface of the carrier; and an electrochemical actuator which changes chemical structure due to an ionic transfer when an electric potential is applied thereto, the actuator being configured to adjust a curvature of the carrier, wherein the curvature is adjustable by applying the electric potential, wherein the method comprises:

inserting the distal end of the carrier into the cochlea with the carrier in a generally straight configuration until the distal end of the carrier reaches the back of the basal turn;

varying the electric potential applied to the actuator to cause change in the chemical structure of the actuator due to the ionic transfer and thereby cause the carrier to at least partially curl; and continuing to insert the carrier and vary the electric potential to vary the curvature of the carrier according to a depth of insertion.

31. A method of inserting a cochlear implant electrode array into a cochlea as claimed in claim 30 wherein the electrochemical actuator is dimensionally changeable by the ionic transfer therein responsive to the application of the electric potential, and the varying of the electric potential applied to the electrochemical actuator causes the ionic transfer therein that causes dimensional changes thereof, the dimensional changes of the actuator applying forces to the carrier which adjust the curvature of the carrier.

32. An implantable electrode array assembly comprising:

an actuator incorporating light sensitive gels in the form of a bimorph or other actuator array for which a change in chemical structure is optically induceable, the actuator being caused to curve when light is applied to the actuator to either straighten a pre-curved cochlear implant electrode array or curve a straight or pre-curved cochlear implant array;

an elongated carrier having a proximal end, a distal end and an inner surface; and a plurality of electrodes mounted within the carrier, at least one of the electrodes having a surface that is adjacent the inner surface of the carrier.

33. An implantable electrode array assembly as claimed in claim 32 wherein the actuator is dimensionally changeable by the ionic transfer therein responsive to the light being applied thereto, and wherein dimensional changes in the actuator apply forces to the carrier that either straighten or curve the carrier.

34. An implantable element for insertion into a human or animal body, comprising:

a flexible body portion;

at least one conductive element; and an electrochemical actuator which changes chemical structure due to an ionic transfer when an electric potential is applied thereto, the actuator being configured to adjust an orientation of the flexible body portion by applying the electric potential to the actuator.

35. An implantable element as claimed in claim 34 wherein the actuator is capable of continuously and incrementally varying the orientation of the flexible body portion between at least a state where the flexible body portion is generally straight and a state wherein the flexible body portion is curved.

36. An implantable element as claimed in claim 34 wherein the implantable element is a steerable part of a cardiac pacemaker, neurostimulator, cochlear implant or wire implant.

37. An implantable element for insertion into a human or animal body as claimed in claim 34 wherein the electrochemical actuator is dimensionally changeable by the ionic transfer therein responsive to the application of the electric potential, and wherein dimensional changes in the actuator apply forces to the carrier that adjust the orientation of the flexible body portion.

38. A method of inserting an implantable element comprising a flexible body portion; at least one conductive element; and an electrochemical actuator which changes chemical structure due to an ionic transfer when an electric potential is applied thereto, the actuator being configured to adjust an orientation of the flexible body portion, the method comprising:

inserting one end of the body portion into a patient's body;

applying the electric potential to the actuator to cause change in the chemical structure thereof due to the ionic transfer, thereby adjusting the orientation of the body portion, the change in the chemical structure of the actuator causing the body portion to change shape which facilitates insertion of the implantable element into the patient's body; and continuing to insert the carrier and vary the electric potential to vary a curvature of the carrier according to a depth of insertion.

39. A method of inserting a cochlear implant electrode array into a cochlea as claimed in claim 38 wherein the electrochemical actuator is dimensionally changeable by the ionic transfer therein responsive to the application of the electric potential, and the varying of the electric potential applied to the electrochemical actuator causes the ionic transfer therein that causes dimensional changes thereof, the dimensional changes of the actuator applying forces to the carrier which adjust the curvature of the carrier.

* * * * *